United States Patent
Read et al.

(10) Patent No.: US 6,569,306 B1
(45) Date of Patent: May 27, 2003

(54) CASSETTE FOR GEL ELECTROPHORESIS HAVING SOLID BUFFER RESERVOIRS

(75) Inventors: Doug Read, San Francisco, CA (US); Lori Hennessy, San Mateo, CA (US); Mohammed Rezaul Islam, Sunnyvale, CA (US)

(73) Assignee: Amersham Pharmacia Biotech, Inc., Piscataway, NJ (US)

( * ) Notice: Subject to any disclaimer, the term of this patent is extended or adjusted under 35 U.S.C. 154(b) by 0 days.

(21) Appl. No.: 09/545,621

(22) Filed: Apr. 10, 2000

(51) Int. Cl.[7] ............... G01N 27/447; G01N 27/453
(52) U.S. Cl. .......................... 204/456; 204/616
(58) Field of Search ..................... 204/466, 456, 204/606, 616

(56) References Cited

U.S. PATENT DOCUMENTS

| | | | |
|---|---|---|---|
| 3,407,133 A | * 10/1968 | Oliva et al. ............... | 204/616 |
| 4,415,418 A | * 11/1983 | Turre et al. ............... | 204/466 |
| 4,828,670 A | 5/1989 | Sarrine ....................... | 204/616 |
| 4,892,639 A | 1/1990 | Sarrine et al. ............. | 204/616 |
| 5,045,164 A | * 9/1991 | Tansamrit et al. .......... | 424/423 |
| 5,851,370 A | 12/1998 | Maracas et al. ............ | 204/450 |
| 5,989,400 A | 11/1999 | Islam ......................... | 204/466 |

FOREIGN PATENT DOCUMENTS

| | | |
|---|---|---|
| GB | 2 276 008 | 9/1994 |
| WO | WO 96/24687 | 8/1996 |

* cited by examiner

*Primary Examiner*—Jill Warden
*Assistant Examiner*—Alex Noguerola
(74) *Attorney, Agent, or Firm*—Royal N. Ronning, Jr.; Stephen G. Ryan

(57) ABSTRACT

A cassette and electrophoretic gel assembly includes a non-conductive cassette, two solid buffer reservoirs, and an agarose gel. The assembly is disposable, and the sample wells on the gel are in standard microtiter plate format. The configuration is such that the gel is continuously in electrical contact with the electrodes in operation despite the production/migration of water and other exudates.

14 Claims, 4 Drawing Sheets

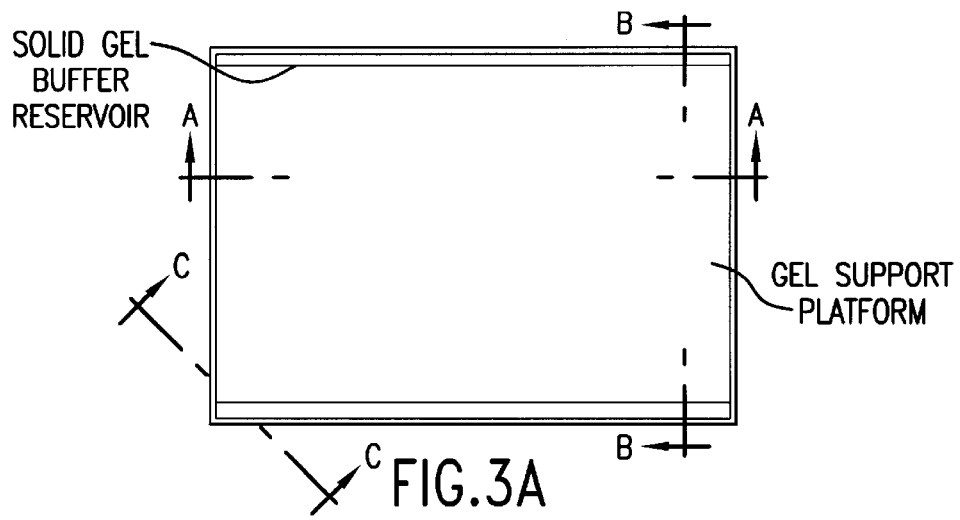
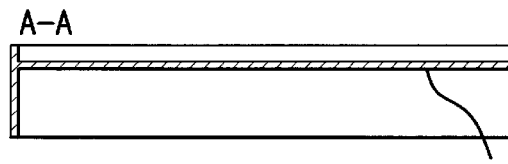
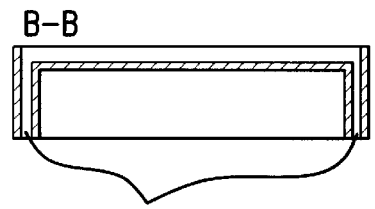
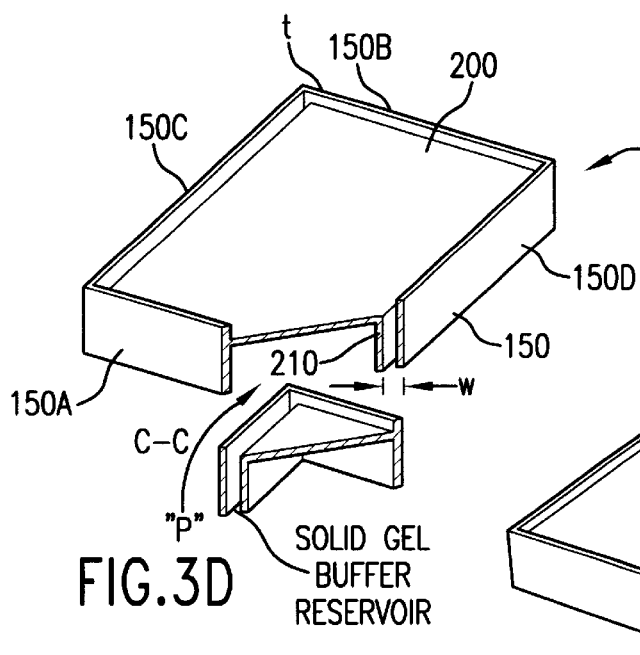
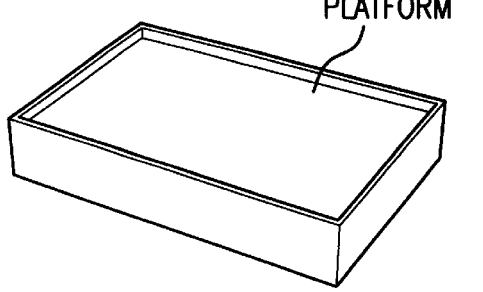

CASSETTE FOR GEL ELECTROPHORESIS HAVING SOLID BUFFER RESERVOIRS

FIELD OF THE INVENTION

The present invention relates to equipment used in bufferless gel electrophoresis.

BACKGROUND OF THE INVENTION

The volume of PCR reactions has grown dramatically as new applications are developed for use in many research areas. In many cases, the amplified product is to be used for further analysis, such as sequencing or in micro-array experiments. Because these types of analysis are both time consuming and expensive, it is more efficient to interrogate the PCR reaction results for amplified product before initiating any further analysis. The easiest and least expensive way to check for successful amplification is to run the product on an agarose gel for a few millimeters.

Conventional electrophoretic screening uses large format (approximately 15–25 cm by 20–30 cm) horizontal submarine agarose gels with multiple combs to form ranks of wells 4 to 8 centimeters apart. This format is expensive in both labor and materials. Moreover, this method is inconvenient for loading and analysis when the sample handling and reactions are performed in microtiter plates (96 wells on 9 mm centers or less). Because the conventional electrophoresis units are difficult to assemble and use, it is much more efficient to run as many samples as possible per gel. However, it is more convenient to analyze the results if the image of the gel maps directly to the layout of the samples on the microtiter tray. With the larger gels, therefore, there is a tradeoff between loading only twelve samples per row, analogous to standard microtiter plate layout (thereby simplifying analysis but wasting gel space) and filling the gel with as many rows as possible (which is more time efficient but complicates analysis).

Furthermore, in agarose gel and buffer strip systems, endosmotic flow of water across fixed anions in the agarose matrix draws water out of the anode and pumps it to the cathode, thus drying and shrinking one end and forming a puddle of liquid on the surface at the other end. In some cases, the gels may also deteriorate at the anode due to hydroxide ions which are generated there. As known by those of skill in the art, it is important that electrical contact be maintained despite potentially deleterious accumulation of water and hydroxide ions.

Therefore, there is a need to provide a gel with an array of wells using both the same spacing and format of standard microtiter plates, in which the electrodes successfully maintain electrical contact with the gel. Previous attempts to meet this need have been unsuccessful. A typical electrophoresis unit (such as the GenePhor, by Amersham Pharmacia Biotech, in San Francisco, Calif.) is capable of giving high-resolution analysis of relatively small numbers of samples. Such a unit is ill-fitted for a fast, comparatively crude analysis such as those which would benefit post-PCR analysis. Generally, units such as these are large, complex to use, slow (due to high resolution), and require complex assembly as described hereinabove.

Several groups have tried to address the difficulty of retaining electrode contact during electrolysis. In Sarrine et al (U.S. Pat. No. 5,637,203, the contents of which are hereby incorporated by reference as if recited in full herein), the gel is placed over a set of pin-type electrodes that protrude through holes in the gel and a gasketed support sheet, making contact with the gel outside of a moulded buffer strip. The holes provide a vent for the gases produced in electrolysis and a means for maintaining contact despite the endosmotic effects. Sarrine et al specifically teaches that a covered hole with the electrode making contact from below is not desirable because it traps electrolysis gas, causing the gel to float off of its support tray. Earlier patents (e.g. U.S. Pat. Nos. 5,045,164 and 4,975,173 by Tansamrit et al, the contents of which are incoporated by reference as if recited in full herein) address alternative ways to reduce and divert the fluid generated during electrophoresis away from the area of separation, such as multiple layered buffer block structures, and appropriate placement of serrations at the ends of the gel outside the buffer blocks.

Other groups (U.S. Pat. Nos. 5,582,702 and 5,865,974 by Cabilly et al, the contents of which are hereby incorporated by reference as if recited in full herein) describe a substantially closed cassette for electrophoresis without liquid buffer in which they must deal with the electrolytic gases produced. Their solutions include adding one or more vents in the cassette, providing or generating unfilled volumes into which the gases can be directed, or creating electrodes composed of material that adsorbs or reacts with either or both of the $O_2$ and $H_2$ produced at the electrodes (e.g. aluminum or palladium).

The present invention describes a gel with an array of wells in the microtiter array format that is cast in a disposable cassette substantially the same size as a standard microtiter plate (approximately 85 mm×127 mm×21 mm), and that uses solid buffer strips in lieu of liquid buffer effectively as described in commonly-assigned U.S. Pat. No. 4,874,491 to Stalberg et al the contents of which are hereby incorporated by reference as if recited in full herein. The electrodes advantageously contact the buffer strips, providing continual electrical contact, as well as an escape path for accumulated liquids and gases.

OBJECTS AND SUMMARY OF THE PRESENT INVENTION

In view of the foregoing, it is an object of the present invention to provide an apparatus for basic, inexpensive and convenient agarose gel electrophoresis of many samples.

It is a further object of the present invention to provide a disposable apparatus for gel electrophoresis which corresponds to standard microtiter plates to facilitate loading and analysis.

It is an additional object of the present invention to provide a bufferless system to run electrophoresis on agarose gels.

An additional object of the present invention is to provide a cassette and gel assembly which enables the user to analyze the results of the run within the cassette.

It is a further object of the present invention to provide an electrophoretic gel system which has electrode-contact surfaces substantially on the bottom yet allows potentially deleterious by-products of electrophoresis to escape.

These and other objects are satisfied by the present invention which is directed to a bufferless gel electrophoresis system which is configured to successfully run electrophoresis gels in standard microtiter plates. In particular, a first aspect of the present invention is directed toward a cassette and gel assembly for electrophoresis including a non conductive cassette, two solid buffer reservoirs, and a gel which contains a plurality of wells adapted to contain a plurality of samples, wherein the cassette is adapted to position the gel and reservoirs such that the electrodes of an electrophoretic device will contact the bottom surface of the gel to permit an electrophoretic procedure to be run. A variety of arrangements of the wells are contemplated, as well as a variety of geometries for the cassette.

BRIEF DESCRIPTION OF THE DRAWINGS

FIG. 3 is a cutoff perspective view of a cassette embodiment according to the present invention.

DETAILED DESCRIPTION OF THE PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity.

Figure 1:
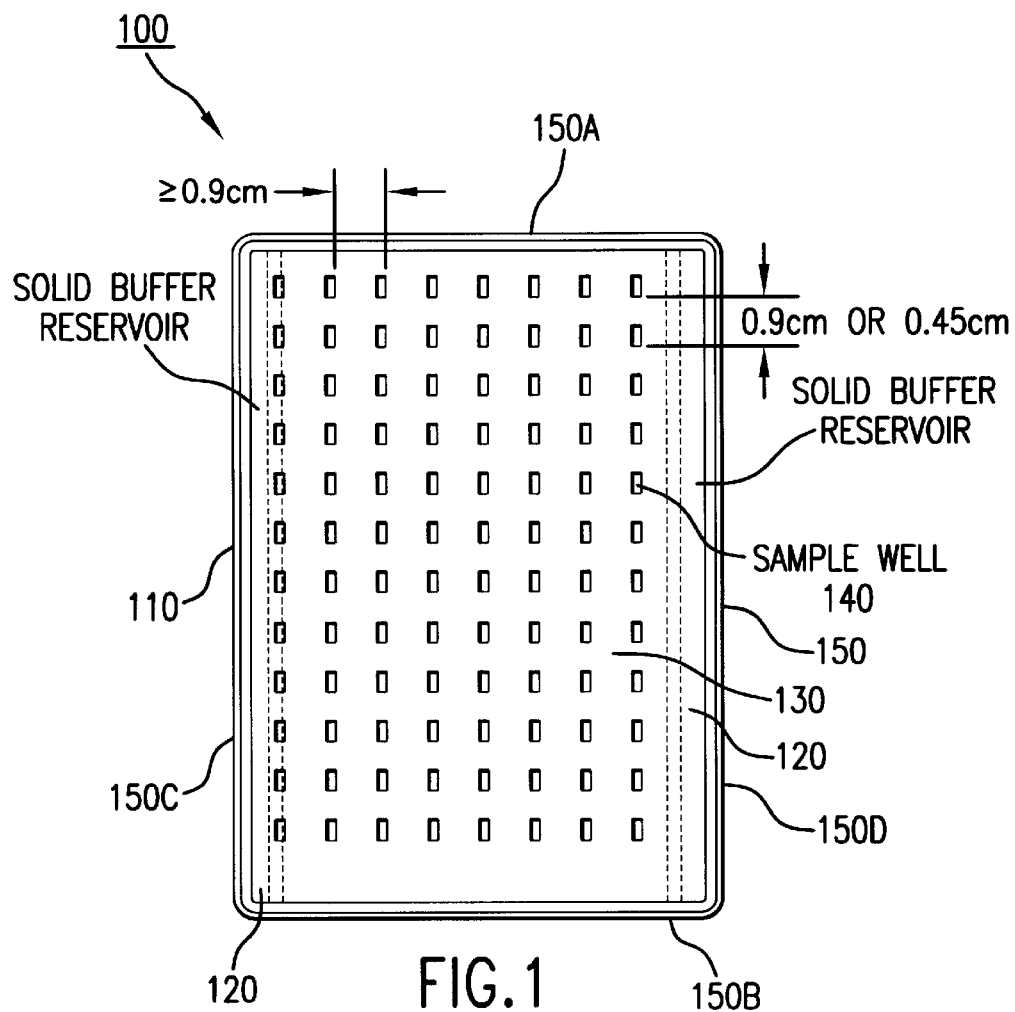
FIG. 1 is a top view of a preferred embodiment according to the present invention.
Figure 2:
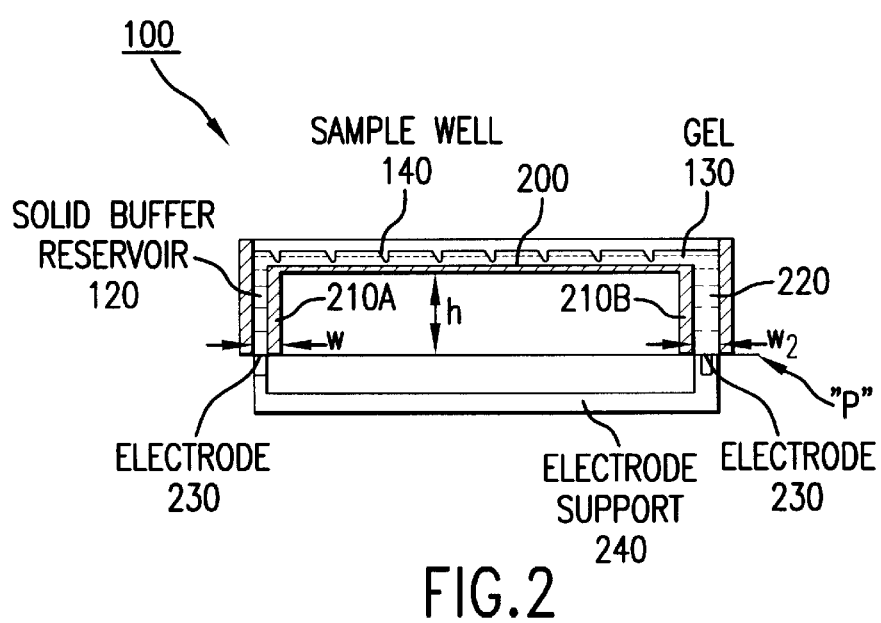
FIG. 2 is a cutoff side view of a preferred embodiment according to the present invention.

Referring to the drawings, the cassette and gel assembly 100 of the present invention is shown in FIG. 1. As shown, the cassette and gel assembly 100 comprises a cassette 110, two solid buffer reservoirs 120, and an agarose gel 130. As FIG. 1 shows, the agarose gel 130 preferably contains 96 sample wells 140, in an 8×12 matrix, plus one or two additional row(s) of 8 wells in which to place electrophoresis standards. The additional row(s) of wells advantageously allow(s) the user to run standards without using up wells in the original microtiter reaction plate. More preferably, the rows of 8 wells 140 are spaced between 1 and 10 mm apart. Most preferably, the rows of 8 wells 140 are spaced 4.5 or 9 mm apart, which corresponds to the spacing on standard microtiter plates. The columns are similarly preferably spaced between 1 and 10 mm apart, and more preferably 4.5 or 9 mm apart. This spacing advantageously allows automated equipment designed to load and manipulate microtiter plates to additionally load and handle the gels. The wells themselves 140 at the gel-air interface (top) are preferably substantially rectangular in shape as shown in FIGS. 1 and 2, to provide a sizeable target for the pipette tips when loading the gel yet provide a substantial surface area on the "starting line" of the gel. Suitable shapes and sizes of wells 140 are well known in the art.

The gel cassette 110 preferably comprises a contiguous arrangement of four laterally extending outer sides 150A–150D which form a frame 150 as shown in FIG. 3. Preferably, the sides of the frame 150 are situated and oriented such that they are in opposing pairs 150A, 150B and 150C, 150D, thereby defining a substantially rectangular geometry. Preferably, the rectangular frame 150 is sized to be approximately substantially that of a standard microtiter plate (commonly approximately 85 mm×127 mm×21 mm).

In one preferred embodiment, a gel support platform 200 horizontally extends from one outer side to its opposing outer side (between one pair of opposing sides). More preferably, the gel support platform 200 extends between the two shorter sides 150A, 150B thereby providing a shelf supported by two walls of the frame 150A, 150B at its ends. Preferably, the gel support platform 200 is additionally supported by two vertically extending shelf supports 210A, 210B. These shelf supports 210A, 210B preferably extend between one opposing pair of sides 150A, 150B parallel to and a distance "$w_1$," and "$w_2$" from the other opposing pair of sides of the frame 150C, 150D as shown in FIGS. 2 and 3. Also as shown in FIG. 3, the gel support platform 200 preferably is positioned vertically below the top edge of the cassette 110 "t" such that the gel support platform 200 is recessed. More preferably, the gel support platform 200 is recessed from the top of the cassette "t" at least approximately 4 mm, such that when an agarose gel 130 is placed on top of the gel support platform 200, the gel 130 does not protrude beyond the top "t." Agarose gels 130 as known in the art, are generally between 3 and 4 mm high.

Figure 4B:
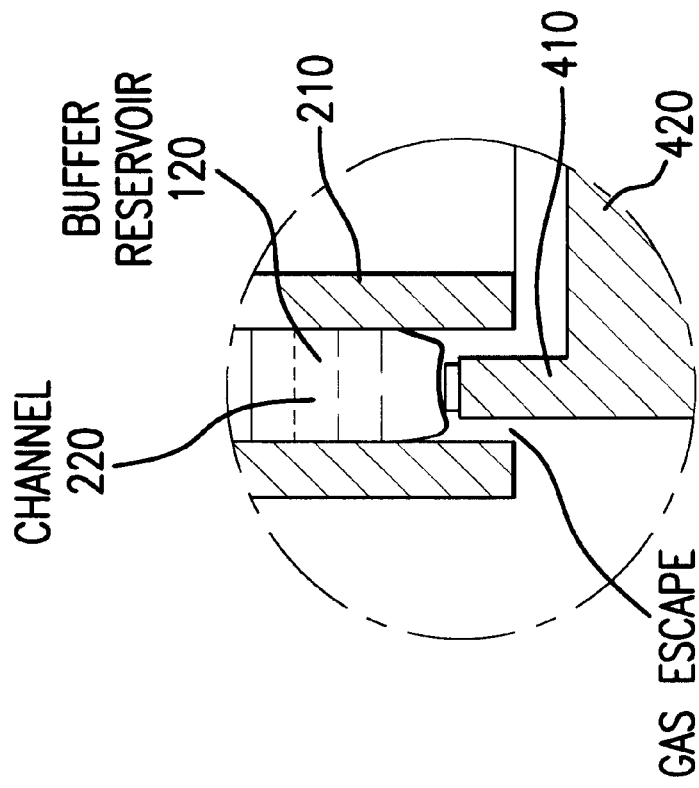
FIG. 4B is an enlarged cutoff view of the electrode-gel contact surface on the anode after electrophoresis has commenced, according to the present invention.
Figure 4A:
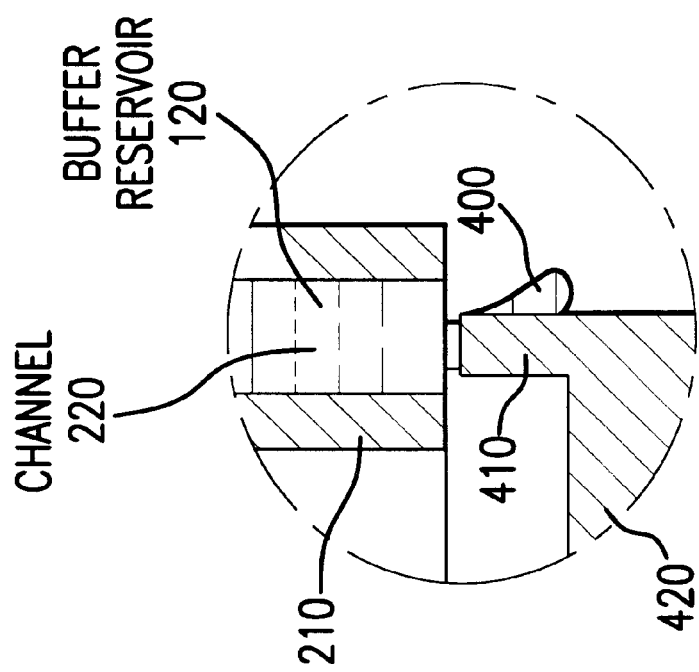
FIG. 4A is an enlarged cutoff view of the electrode-gel contact surface on the cathode according to one embodiment of the present invention.

Preferably the shelf supports 210A, 210B extend exactly from the plane defined by the bottom of the frame "P" up to the gel support platform 200. Advantageously, as shown in FIG. 2, in this configuration, the shelf supports 210A, 210B and an opposing pair of outer walls 150C, 150D define two channels 220 into which solid buffer reservoirs 120 can be placed. Additionally, the solid buffer reservoir 120 is preferably substantially large enough to hold a sufficient volume of buffer for an electrophoresis run. Preferably, this volume is at least about 1 mL. More preferably, the volume of the solid buffer reservoir is between 2 and 10 mL, and most preferably it is between 4 to 7 mL. Notably, the solid buffer reservoirs 120 on a single cassette do not have to be the same volume, and it is advantageous that the solid buffer reservoir 120 on the anode be of larger volume than that on the cathode due to endosmosis. The dimensions of the solid buffer reservoir can be changed such that it may hold more or less buffer, depending on the length of time that the gel is to run. Both the widths "$w_1$," "$w_2$" and height "h" of the solid buffer reservoir may be changed to alter the resulting volume of the solid buffer reservoir while remaining within the scope of the present invention. However, it may be advantageous to keep the widths "$w_1$," "$w_2$" of the solid buffer reservoirs between 2 mm and 4 mm to maximize the resulting field of view yet provide sufficient solid buffer volume to complete the run. More preferably, the solid buffer reservoirs are dimensioned such that when the cassette and gel assembly is placed on an electrode 230/electrode support 240 assembly, there is a gap in the horizontal plane as shown in FIG. 2 between the electrode 230 and the sides of the channel 220. This gap advantageously allows water 400 and hydroxide ions to preferably exit the system without disturbing the electrical contact between the electrodes 230 and the agarose gel 130 as shown in FIG. 4A and discussed herein below.

The agarose gel 130 preferably can be placed in the cassette 110 such that it is substantially supported by the gel support platform 200 in the cassette 110, as shown in FIG. 2. More preferably, as shown in FIG. 2, the agarose gel 130 is in fluid communication with the two solid buffer reservoirs 120. In a more preferred embodiment, the agarose gel 130 contacts the solid buffer reservoirs 120 substantially from the top as shown in FIG. 2 such that the gravitational force on the agarose gel 130 continually forces the gel 130 to contact the solid buffer reservoirs 120. Advantageously, therefore, as water is pumped out of the anode due to electroendosmosis, thereby causing the solid buffer reservoir 120 to shrink, the gel 130 settles and therefore maintains contact with the solid buffer reservoir 120.

Preferably, the cassette and gel assembly 100 promote ease of use. To further facilitate ease of use, the cassette 110 preferably comprises a UV-transmitting non-conductive material. This advantageously allows the end user to view the results, after the gel electrophoresis is complete, without removing the agarose gel 130 from the cassette and gel assembly 100. For example, a UV-transmitting acrylic or any other UV-transmitting plastic can be used as cassette material. More preferably, the cassette 110 comprises a relatively inexpensive UV-transmitting non-conductive material, such that the entire gel and cassette assembly 100 can be discarded after the agarose gel has been run. Since the user does not have to re-use the cassette 110, the user can also advantageously minimize setup (cassette and gel assemblies can be provided preassembled) and cleanup before and after each run.

Figure 5:
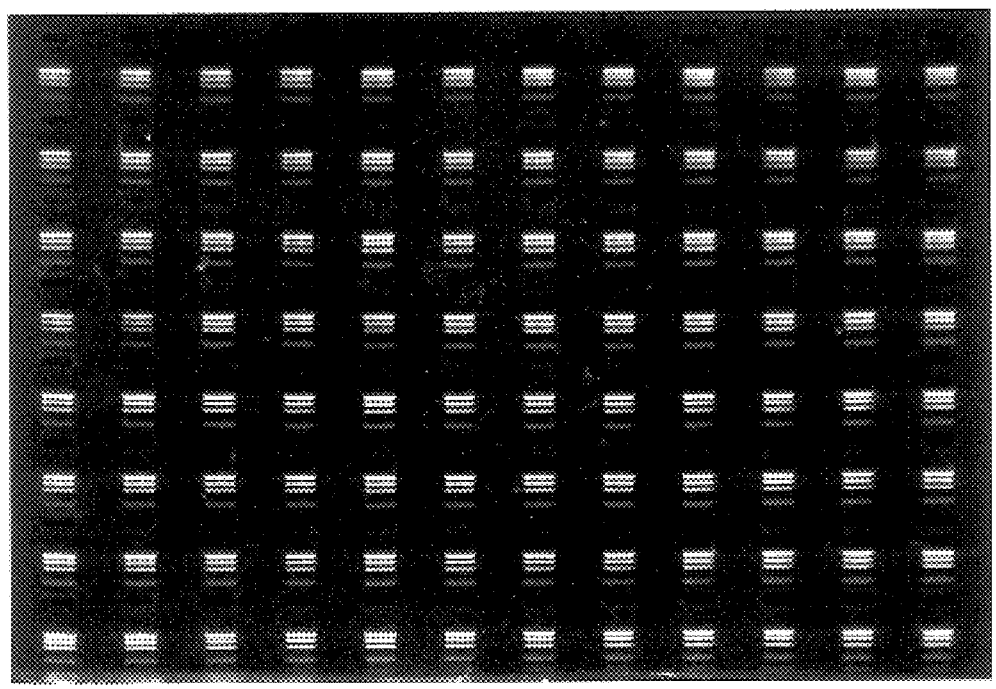
FIG. 5 depicts the results of an electrophoresis run performed by one embodiment of the present invention.

An embodiment of the present invention has been used to successfully run agarose gel electrophoresis on commercial DNA molecular size standards ranging from 100 bp to greater than 3000 bp. As shown in FIG. 5, the cassette and gel assembly 100 according to the present invention enables a user to successfully determine in a short amount of time (the run illustrated in FIG. 5 took 6 minutes at 100V) the presence of product in each of the wells 140.

In operation, the wells 140 in the gel 130 are filled with samples to be analyzed. The entire gel and cassette assembly 100 is then placed on an electrophoresis device such that the electrodes 230 are in contact with the agarose gel 130 as shown in FIG. 4A. As the run proceeds, the solid buffer reservoir 120 shrinks at the anode as water is endosmotically pumped to the cathode. Because the electrode 230 preferably makes contact with the solid buffer reservoir 120 from the bottom, the weight of the gel and cassette assembly 100 forces the electrode 230 to maintain contact with the solid buffer reservoir 120. Preferably the electrode support 240 has a substantially vertically recessed portion (with respect to the electrode) as shown in FIGS. 2 and 4B, to form a vertical upstanding portion 410 and a horizontal portion 420 of the electrode support 240. Preferably, the walls of the channel 220 are preferably configured such that its widths "$w_1$," "$w_2$" are larger than the width of the electrode 230 and vertical upstanding portion of the electrode support 410. In this configuration, as the solid buffer reservoir 120 shrinks at the anode, the entire gel and cassette assembly 100 is not impeded from vertically dropping. Furthermore, this configuration advantageously allows excess water 400 and gases to escape out the bottom of the gel and cassette assembly 100 between the walls of the channel 220 and the electrode 230/vertical upstanding portion of the electrode support 410 as shown in FIG. 4A.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. An electrophoresis device comprising
   (a) (i) a non-conductive cassette having a solid buffer reservoir at each of two opposing ends of the cassette, each buffer reservoir having a top surface and a bottom surface, and (ii) a gel having a top surface and a bottom surface, the bottom surface of the gel being in contact with the top surface of the buffer reservoirs; and
   (b) an electrode support supporting two electrodes,
   wherein the cassette is adapted to position said gel and buffer reservoirs such that the electrodes of the electrode support will only contact the bottom surface of the buffer reservoirs to permit an electrophoretic procedure to be run, and wherein said gel contains a plurality of wells adapted to contain a plurality of samples.

2. The assembly of claim 1 wherein said gel is an agarose gel.

3. The assembly of claim 1 wherein said gel contains at least 96 wells arranged in a rectangular geometry having rows containing 8 wells and columns containing at least 12 wells.

4. The assembly of claim 3 wherein the columns contain 13 or 14 wells.

5. The assembly of claim 3 wherein the spacing between individual wells within each row and column corresponds to the spacing on a standard microtiter plate.

6. The assembly of claim 1 wherein the cassette comprises a contiguous arrangement of 4 laterally extending outer sides arranged to form a frame.

7. The assembly of claim 6 wherein said sides are sized and arranged so that the frame has a substantially rectangular geometry.

8. The assembly of claim 7 which further includes a gel support platform which extends between one pair of opposing sides.

9. The assembly of claim 8 wherein said platform extends between the pair of sides which have the shorter size.

10. The assembly of claim 9 wherein said platform is recessed below the top surface of said cassette.

11. The assembly of claim 1 wherein said solid buffer reservoirs contain at least 1 ml of buffer.

12. The assembly of claim 11 wherein said solid buffer reservoirs contain different amounts of buffer.

13. The assembly of claim 1 wherein said cassette is comprised of a non-conductive material which is capable of transmitting ultraviolet light.

14. A method of electrophoretically analyzing a plurality of samples with the electrophoresis device of claim 1 comprising the steps of loading the plurality of wells of the cassette with the samples to be analyzed, engaging the cassette with the electrode support such that the electrodes contact the bottom surface of the buffer reservoirs, running the electrophoresis for the desired amount of time, and viewing the results.

* * * * *